(12) United States Patent
Ross

(10) Patent No.: US 6,335,330 B1
(45) Date of Patent: *Jan. 1, 2002

(54) CRYSTALLINE PHARMACEUTICAL PRODUCT

(75) Inventor: Stephen Torey Ross, Berwyn, PA (US)

(73) Assignee: SmithKline Beecham Corporation, Philadelphia, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/254,305

(22) PCT Filed: Aug. 29, 1997

(86) PCT No.: PCT/US97/15292

§ 371 Date: Mar. 3, 1999

§ 102(e) Date: Mar. 3, 1999

(87) PCT Pub. No.: WO98/09629

PCT Pub. Date: Mar. 12, 1998

Related U.S. Application Data

(60) Provisional application No. 60/025,369, filed on Sep. 3, 1996.

(51) Int. Cl.$^7$ .................. A61K 31/5513; C07D 223/16
(52) U.S. Cl. ........................................ 514/221; 540/513
(58) Field of Search ........................... 540/513; 514/221

(56) References Cited

U.S. PATENT DOCUMENTS

| 5,693,636 A | 12/1997 | Bondinell et al. | .......... 514/221 |
| 5,939,412 A | 8/1999 | Bondinell et al. | .......... 514/213 |

FOREIGN PATENT DOCUMENTS

| WO | WO 93/00095 | 1/1993 |
| WO | WO 94/14776 | 7/1994 |
| WO | WO 95/18619 | 7/1995 |
| WO | WO95/18619 | 7/1995 |

*Primary Examiner*—Fiona T. Powers
(74) *Attorney, Agent, or Firm*—Charles M. Kinzig

(57) ABSTRACT

This invention provides (S)-7-[(4,4'-bipiperidin-1-yl) carbonyl]-2,3,4,5-tetrahydro-4-methyl-3-oxo-1H-1,4-benzodiazepine-2-acetic acid, hydrochloride, processes for its preparation and methods for its use.

17 Claims, No Drawings

CRYSTALLINE PHARMACEUTICAL PRODUCT

This application claims benefit of provisional application Ser. No. 60/025,369 filed Sep. 3, 1996. This application is a 371 of PCT/US97/15292 filed Aug. 29, 1997.

FIELD OF THE INVENTION

This invention relates to a crystalline salt form of (S)-7-[(4,4'-bipiperidin- 1-yl)carbonyl]-2,3,4,5-tetrahydro-4-methyl-3-oxo-1H-1 ,4-benzodiazepine-2-acetic acid, its preparation and use as a therapeutic substance.

BACKGROUND

The compound (S)-7-[(4,4'-bipiperidin-1-yl)carbonyl]-2,3,4,5-tetrahydro-methyl-3-oxo-1H-1,4-benzodiazepine-2-acetic acid, given by formula (I), and procedures

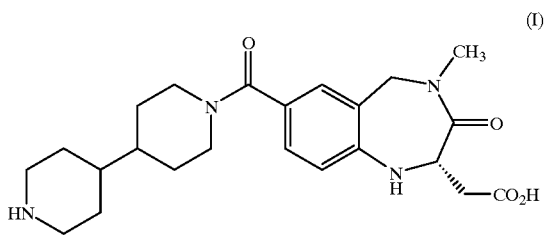

for preparing such compound, its trifluoroacetic acid and sodium salts are disclosed in WO 95/18619 (PCT/U.S. Ser. No. 95/00248, SmithKline Beecham Corp.). Since this compound has both a basic and acidic center, it may exist as either an acid addition salt or basic addition salt. If neither an acid nor a basic addition salt is formed, it may exist as an internal salt or zwitterion. This compound is an inhibitor of the GPIIbIIIa (fibrinogen) receptor on platelets and it acts to inhibit platelet aggregation. Thus, the compound is useful for treating such ailments as stroke, myocardial infarction, thrombosis, embolism, and restenosis following angioplasty. The zwitterion and trifluoroacetate salt prepared according to WO 95/18619 possess undesirable characteristics for preparing pharmaceutical formulations of this compound for commercial sale. The zwitterion is hygroscopic and tends to have a variable water content, equilibrating toward a species which takes up about six molar equivalents of water. This may cause difficulty in milling and mixing to create pharmaceutical compositions. The trifluoroacetate salt is not thermally stable for an extended period which impairs its shelf life.

Accordingly, a stable form of the compound which possesses desirable physical characteristics is needed.

SUMMARY OF THE INVENTION

This invention comprises a stable hydrochloride salt of (S)-7-[(4,4'-bipiperidin-1-yl)carbonyl]-2,3,4,5-tetrahydro-4-methyl-3-oxo-1H-1,4-benzodiazepine-2-acetic acid.

In another aspect, this invention comprises a stable pharmaceutical composition of (S)-7-[(4,4'-bipiperidin-1-yl)carbonyl]-2,3,4,5-tetrahydro-4-methyl-3-oxo-1H-1,4-benzodiazepine-2-acetic acid, hydrochloride.

In yet another aspect, this invention comprises a method of antagonizing the fibrinogen receptor for preventing or treating diseases wherein platelet aggregation or the binding of ligand to the fibrinogen receptor is a factor.

DETAILED DESCRIPTION

It has now been found that (S)-7-[(4,4'-bipiperidin-1-yl)carbonyl]-2,3,4,5-tetrahydro-4-methyl-3-oxo-1H-1,4-benzodiazepine-2-acetic acid may be prepared as a hydrochloride salt which is crystalline, stable and possesses a consistent water content. Its preparation and physical properties appear to be consistent and reproducible, which make it particularly useful for use in a commercial product.

The present invention provides (S)-7-[(4,4'-bipiperidin-1-yl)carbonyl]-2,3,4,5-tetrahydro-4-methyl-3-oxo-1H-1,4-benzodiazepine-2-acetic acid, hydrochloride, formula (I), as a novel material, and, in particular, as a pharmaceutically acceptable form. The material crystallizes preferably with one mole of HCl, and appears to exist in a generally anhydrous form. Although small amounts of water may be detected by Karl Fischer analysis, this is generally less than 1–2% w/w of the drug substance, and it appears to be consistent irrespective of the storage conditions. The hydrochloride does not appear to exist in polymorphic forms, but in a single microcrystalline aggregate form ranging from 10 to 250 microns. Accordingly, the hydrochloride salt form offers significant advantages for bulk material consistency, handling, and formulation. In addition, the hydrochloride salt form exhibits enhanced dissolution and solubility in water.

In a preferred aspect, this invention provides (S)-7-[(4,4'-bipiperidin-1-yl)carbonyl]-2,3,4,5-tetrahydro-4-methyl-3-oxo-1H-1,4-benzodiazepine-2-acetic acid, hydrochloride in substantially pure form.

The present invention also provides a process for preparing (S)-7-[(4,4'-bipiperidin-1-yl)carbonyl]-2,3,4,5-tetrahydro4-methyl-3-oxo-1H-1,4-benzodiazepine-2-acetic acid, hydrochloride which comprises forming a solution of (S)-7-[(4,4'-bipiperidin-1-yl)carbonyl]-2,3,4,5-tetrahydro-4-methyl-3-oxo-1H-1,4-benzodiazepine-2-acetic acid, hydrochloride and crystallizing the hydrochloride salt from solution by precipitation or recrystallization. The solution may be prepared in any conventional manner, such as by dissolving the (S)-7-[(4,4'-bipiperidin-1-yl)carbonyl]-2,3,4,5-tetrahydro-4-methyl-3-oxo-1H-1,4-benzodiazepine-2-acetic acid, or a suitable salt, in a suitable solvent, and adding hydrogen chloride as a gas, or dissolved in a second solvent to the solution. The second solvent may be the same or different from that used in the original solution. Preferably the second solvent will be miscible with the solvent for the benzodiazepine. Water is a useful solvent. Alcohols, especially methanol, ethanol, and isopropanol, are particularly preferred organic solvents for dissolving the hydrochloric acid and making the hydrochloride salt.

The hydrochloride salt may be precipitated from the solution by adding a solvent in which the salt if less soluble than the solvent in which the salt is prepared or by inducing crystallization, for instance by chilling the solution, adding a co-solvent, adding a seed crystal, or merely allowing the solution to stand. Alternatively, the hydrochloride salt may be precipitated by concentrating the solution of the hydrochloride salt, e.g., removing the solvent(s), such as by evaporation. In another alternative, the solvent may be removed, and the residue may be treated with another solvent, or mixture of solvents, to induce crystallization.

Although the process is preferably carried out starting with a solution of the zwitterionic form of (S)-7-[(4,4'-bipiperidin-1-yl)carbonyl]-2,3,4,5-tetrahydro-4-methyl-3-oxo-1H-1,4-benzodiazepine-2-acetic acid, the hydrochloride may be prepared using other salts, for instance an acid addition salt, such as the acetate or trifluoroacetate salt, or a basic addition salt, such as an alkali metal (e.g., lithium, sodium or potassium) or organic amine salt.

In one embodiment, the (S)-7-[(4,4'-bipiperidin-1-yl)carbonyl]-2,3,4,5-tetrahydro-4-methyl-3-oxo-1H-1,4- benzodiazepine-2-acetic acid is suspended in water, and titrated with an aqueous solution of hydrochloric acid to a pH of about 2–3. During the addition of acid, the solid dissolves to give a clear solution. It is important to avoid an excess of the acid, about one equivalent is desired, to produce a stable and readily crystallizable salt. Evaporation of the water yields a crude hydrochloride salt which may be recrystallized from an appropriate solvent, such as ethanol to yield a purified hydrochloride salt.

(S)-7-[(4,4'-bipiperidin-1-yl)carbonyl]-2,3,4,5-tetrahydro-4-methyl-3-oxo-1H-1,4-benzodiazepine-2-acetic acid as a zwitterion may be prepared according to the procedures set forth in WO 95/18619 and WO 97/24336 (PCT/IB96/01502, SmithKline Beecham) which are incorporated herein by reference as though fully set forth.

This invention further provides a pharmaceutical composition which comprises (S)-7-[(4,4'-bipiperidin-1-yl) carbonyl]-2,3,4,5-tetrahydro-4-methyl-3-oxo-1H-1,4-benzodiazepine-2-acetic acid, hydrochloride and a pharmaceutically acceptable carrier. Accordingly, (S)-7-[(4, 4'-bipiperidin- 1 -yl)carbonyl]-2,3,4,5-tetrahydro4-methyl-3-oxo-1H-1,4-benzodiazepine-2-acetic acid, hydrochloride may be used in the manufacture of a medicament. Pharmaceutical compositions may be formulated as a solution or powder for parenteral administration. Powders may be reconstituted by addition of a suitable diluent or other pharmaceutically acceptable carrier prior to use. The liquid formulation may be a buffered, isotonic, aqueous solution. Examples of suitable diluents are normal pyrogen-free water, isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Preferably, the (S)-7-[(4,4'-bipiperidin-1-yl)carbonyl]-2, 3,4,5-tetrahydro-4-methyl-3-oxo-1H-1,4-benzodiazepine-2-acetic acid, hydrochloride may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies, but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule. Capsules and tablets are preferred dosage forms.

For rectal administration, the compound may also be combined with excipients such as cocoa butter, glycerin, gelatin or polyethylene glycols and molded into a suppository.

This invention also provides a method of inhibiting platelet aggregation and clot formation in a mammal, especially a human, which comprises the internal administration of (S)-7-[(4,4'-bipiperidin-1-yl)carbonyl]-2,3,4,5-tetrahydro-4-methyl-3-oxo-1H-1,4-benzodiazepine-2-acetic acid, hydrochloride and a pharmaceutically acceptable carrier. Indications for such therapy include acute myocardial infarction (AMI), deep vein thrombosis, pulmonary embolism, dissecting aneurysm, transient ischemia attack (TIA), stroke and other infarct-related disorders, and unstable angina. The compounds of this invention are also useful for preventing restenosis of an artery or vein in a mammal following angioplasty. Chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venom and immune diseases, are likely to be responsive to such treatment. These compounds are also believed to be useful for adjunct therapy following angioplasty.

The compound of this invention may also be favorably administered with other agents which inhibit platelet aggregation. For instance, the (S)-7-[(4,4'-bipiperidin-1-yl) carbonyl]-2,3,4,5-tetrahydro-4-methyl-3-oxo-1H-1,4-benzodiazepine-2-acetic acid, hydrochloride may be administered with compounds of the class of cyclooxygenase inhibitors, thromboxane antagonists, thromboxane synthetase inhibitors, heparins, thrombin inhibitors, ADP receptor inhibitors/antagonists and ticlopidine. Examples of such agents are aspirin, warfarin and clopidogrel.

The pharmaceutical composition is administered either orally or parenterally to the patient, in a manner such that the concentration of (S)-7-[(4,4'-bipiperidin-1-yl)carbonyl]-2,3, 4,5-tetrahydro-4-methyl-3-oxo-1H-1,4-benzodiazepine-2-acetic acid, hydrochloride in the plasma is sufficient to inhibit platelet aggregation, or other such indication. The pharmaceutical composition containing the drug is administered at a dose between about 0.2 to about 50 mg/kg of active compound in a manner consistent with the condition of the patient. For acute therapy, parenteral administration is preferred. For persistent states of hyperaggregability, an intravenous infusion of the compound in 5% dextrose in water or normal saline is most effective, although an intramuscular bolus injection may be sufficient.

For chronic, but noncritical, states of platelet aggregability, oral administration of a capsule or tablet, or a bolus intramuscular injection is suitable. The compound is administered one to four times daily at a level of about 0.4 to about 50 mg/kg to achieve a total daily dose of about 0.4 to about 200 mg/kg/day. Preferably, it is administered about two times daily at a level of about 50 to 600 mg/dose.

This invention further provides a method for inhibiting the reocclusion or restenosis of an artery or vein following fibrinolytic therapy, which comprises internal administration of (S)-7-[(4,4'-bipiperidin-1-yl)carbonyl]-2,3,4,5-tetrahydro-4-methyl-3-oxo-1H-1,4-benzodiazepine-2-acetic acid, hydrochloride and a fibrinolytic agent. Administration of the compound in fibrinolytic therapy either prevents reocclusion completely or prolongs the time to reocclusion.

Methods for assessing the ability of the compound of this invention to inhibit the fibrinogen receptor and inhibit platelet aggregation are common in the art and may be found for instance in WO 95/18619 (PCT/U.S. Ser. No. 95/00248, SmithKline Beecham Corp.) and WO 94/14776 (PCT/U.S. Ser. No. 93/12436, SmithKline Beecham Corp.).

The examples which follow are intended to in no way limit the scope of this invention, but are provided to illustrate how to make and use the compounds of this invention. Many other embodiments will be readily apparent and available to those skilled in the art.

EXAMPLES

In the Examples, all temperatures are in degrees Centigrade. Mass spectra were performed using fast atom bombardment (FAB) or electro-spray (ES) ionization. Melting points were taken on a Thomas-Hoover capillary melting point apparatus and are uncorrected. Optical rotations were determined on a Perkin Elmer 241 polarimeter, using a 10 cm path length cell. The melting point and optical rotation of samples may vary upon repeated experiments, but they are reproducible within about 5%.

NMR were recorded at 250 MHz using a Bruker AM 250 spectrometer, unless otherwise indicated. Chemical shifts are reported in ppm (5) downfield from tetramethylsilane. Multiplicities for NMR spectra are indicated as: s=singlet, d=doublet, t=triplet, q=quartet, m=multiplet, dd=doublet of doublets, dt=doublet of triplets etc. and br indicates a broad signal. J indicates the NMR coupling constant in Hertz.

EXAMPLE 1

Preparation of (S)-7-[(4,4'-bipiperidin-1-yl)carbonyl]-2,3,4,5-tetrahydro-4-methyl-3-oxo-1H-1,4-benzodiazepine-2-acetic acid, hydrochloride (S)-7-[(4,4'-bipiperidin-1-yl)carbonyl]-2,3,4,5-tetrahydro-4-methyl-3-oxo-1H-1,4-benzodiazepine-2-acetic acid, 1.5 hydrate (4.0 g, 9.3 mmol) was suspended in water (20 mL) and stirred. Concentrated (12 N) hydrochloric acid was added dropwise while monitoring the pH of the mixture. The solid material dissolved as the acid was added to yield a yellowish solution, and the pH was lowered to 2.4. The water was evaporated under reduced pressure to yield a glass.(5.0 g). This material was stirred and triturated with absolute ethanol (10 mL) to yield a crystalline solid. The solid was filtered and air-dried to yield the title compound. Mp(ethanol) 292.5–293.5° C. [α]D25° (c 0.5, MeOH) −176.2. Anal. ($C_{23}H_{32}N_4O_4 \cdot HCl$) calcd: C, 59.41; H, 7.15; N, 12.05. found: C, 59.11; H, 7.22; N, 11.67.

Comparison between (S)-7-[(4,4'-bipiperidin-1-yl)carbonyl]-2,3,4,5-tetrahydro-4-methyl-3-oxo-1H-1,4-benzodiazepine-2-acetic acid (zwitterion) and (S)-7-[(4,4'-bipiperidin-1-yl)carbonyl]-2,3,4,5-tetrahydro-4-methyl-3-oxo-1H-1,4-benzodiazepine-2-acetic acid, hydrochloride (HCl Salt).

| Property | Zwitterion | HCl Salt |
| --- | --- | --- |
| Thermal Stability (solid samples, 3 days at 100° C.) | some degradation, increase in organic impurities by 1.3% (hplc, by area) | Stable, no increase in organic impurities |
| Polarized light microscopy | prismatic needle type crystals (100–500 microns) | microcrystalline (10–250 microns) |
| Hygroscopicity (% w/w Karl Fischer analysis) | t = 0    5.6<br>t = 21 days   20.1 | t = 0    0.9<br>t = 21 days   0.8 |

The hydrochloride salt has also been found to be about ten times more soluble in water than the zwitterion.

EXAMPLE 2

Pharmaceutical Composition

For preparing a standard 200 mg capsule containing 20 mg of the active drug product, the following components are used: (S)-7-[(4,4'-bipiperidin-1-yl)carbonyl]-2,3,4,5-tetrahydro-4-methyl-3-oxo-1H-1,4-benzodiazepine-2-acetic acid, hydrochloride (21.7 mg), microcrystalline cellulose N.F. (57.7 mg), magnesium stearate N.F. (2 mg), pregelatinized starch N.F. (q.s. ad 200 mg). All ingredients are screened with a #40 mesh stainless steel screen. A suitable mixer/blender, such as a Paterson Kelly V blender, is charged with an equal portion of the pregelatinized starch, microcrystalline cellulose and the hydrochloride salt, and mixed well. Portions of pregelatinized starch and microcrystalline cellulose are added in geometric increments and mixed. Finally the magnesium stearate is added and blended to produce the final capsule mix which is then filled into a size 2 hard gelatin capsule.

What is claimed is:

1. (S)-7-[(4,4'-bipiperidin-1-yl)carbonyl]-2,3,4,5-tetrahydro-4-methyl-3-oxo-1H-1,4-benzodiazepine-2-acetic acid, hydrochloride.

2. The compound of claim 1 having a melting point of about 291° C.

3. The compound of claim 1 having a negative specific rotation of about 175.

4. A pharmaceutical composition comprising the compound of claim 1 and a pharmaceutically acceptable carrier.

5. A process for preparing the compound of claim 1 which comprises forming a solution of (S)-7-[(4,4'-bipiperidin-1-yl)carbonyl]-2,3,4,5-tetrahydro-4-methyl-3-oxo-1H-1,4-benzodiazepine-2-acetic acid, hydrochloride and crystallizing said hydrochloride salt by precipitation or recrystallization.

6. A method of inhibiting platelet aggregration which comprises administering the compound of claim 1 to a mammal in need thereof.

7. A method of treating myocardial infarction, thrombosis, embolism, stroke and infarct-related disorders, or restenosis following angioplasty, which comprises administering the compound of claim 1.

8. A method for inhibiting the reocclusion or restenosis of an artery or vein following fibrinolytic therapy, which comprises internal administration of a compound according to claim 1 and a fibrinolytic agent.

9. A method for inhibiting platelet aggregation comprising administering a compound according to claim 1, and a cyclooxygenase inhibitor, a thromobxane synthesis inhibitor, a thromboxane antagonist, a heparin, a thrombin inhibitor, an ADP inhibitor.

10. A method for inhibiting platelet aggregation comprising administering a compound according to claim 1 and aspirin, ticlopidine, warfarin or clopidogrel.

11. A method according to claim 6 for treating or preventing myocardial infarction.

12. A method according to claim 6 for treating or preventing unstable angina.

13. A method according to claim 6 for treating or preventing transient ischemia attack.

14. A method according to claim 6 for treating or preventing stroke.

15. A method according to claim 6 for preventing restenosis of an artery or vein following angioplasty.

16. A method for inhibiting platelet aggregation comprising administering a compound according to claim 1 and aspirin.

17. A pharmaceutical composition according to claim 4 comprising a 20 mg unit dose.

* * * * *